United States Patent [19]

Lee

[11] 4,229,179
[45] Oct. 21, 1980

[54] SPECTROPHOTOMETRIC MEASUREMENT IN A CHEMICAL TESTING APPARATUS

[75] Inventor: Lap Y. Lee, Houston, Tex.

[73] Assignee: Hycel, Inc., Houston, Tex.

[21] Appl. No.: 920,863

[22] Filed: Jun. 30, 1978

[51] Int. Cl.² .................... G01N 21/24; G01N 21/26
[52] U.S. Cl. .................... 23/230 R; 422/81;
422/82; 356/246
[58] Field of Search .................... 422/82, 81, 104;
23/230 R; 356/246

[56] References Cited

U.S. PATENT DOCUMENTS

| 3,286,583 | 11/1966 | Ferrari | 422/104 |
| 3,342,019 | 9/1967 | Smythe | 422/82 |
| 3,418,053 | 12/1968 | Pelavin | 422/82 |
| 3,422,667 | 1/1969 | Hrdina | 422/82 |
| 3,480,369 | 11/1969 | Smythe et al. | 422/82 |
| 3,529,896 | 9/1970 | Padawer | 422/82 |
| 3,584,964 | 6/1971 | Najame, Jr. | 422/104 |

Primary Examiner—R. E. Serwin

[57] ABSTRACT

In a spectrophotometric measuring apparatus sample liquid is pumped into a substantially cylindrical cuvette having an internal dimension such that a meniscus of a leading edge of a liquid sample pumped therethrough is maintained. Radiant energy directed through the sample liquid is directed across the path of fluid flow rather than along the length thereof. Consequently, spectrophotometric measurement is performed using a significantly reduced optical pathlength.

16 Claims, 5 Drawing Figures

SPECTROPHOTOMETRIC MEASUREMENT IN A CHEMICAL TESTING APPARATUS

BACKGROUND OF THE INVENTION

The present invention relates to chemical testing apparatus, and more particularly to spectrophotometric apparatus and method therein for measuring optical density of samples.

The present invention is suited for use in automatic chemical analyzers in which aliquots of a fluid sample to be analyzed are each mixed with selected reagents, depending on the substance whose concentration in the aliquot is being tested. After incubation, the reacted contents of a reaction container, hereinafter referred to as a liquid sample, are measured spectrophotometrically. As used herein, spectrophotometrically may mean a form of measurement in which a radiant energy measurement is a function of the concentration of the substance being tested for in the liquid sample. This may include colorimetric, ultraviolet, fluorescent and nephelometric measurement. Examples of such automatic chemical testing apparatus are found in U.S. Pat. Nos. 3,622,279, 4,039,287 and 4,039,288 all issued to John J. Moran and assigned to the assignee herein, the disclosures of which are incorporated herein by reference.

A common form of measuring optical density of a sample is use of the so called flow cell. Liquid sample is pumped through a cuvette defining a tube. Liquid flows in and out of conduits which are positioned perpendicularly with respect to the tube flowpath. Radiant energy is directed along the length of the flowpath, i.e. along the longitudinal axis of the tube through windows at opposite longitudinal ends of the tube. In this manner, the traditional one centimeter pathlength for spectrophotometric measurements to which the automatic analyzer art has, to a degree, standardized is maintained. Examples of such embodiments are found in U.S. Pat. Nos. 3,241,432 to Skeggs et al and 4,052,161 to Atwood et al. These embodiments have a limited range of optical density which they can measure due to the magnitude of the optical pathlength to a great and optical density in the liquid sample may prevent any radiant energy from reaching a detector. While cuvettes having short optical pahtlengths are known (for example type J48 listed in the catalog of Markson Scientific Supply Co., Inc., Carlsbad, Calif.) they are used for other purposes and are totally unsuited to application in systems in which a number of liquid samples are pumped through the cuvette in succession since intersample contamination would result without an intervening cleaning operation that cannot be readily performed while maintaining a high level of sample throughput.

SUMMARY OF THE INVENTION

It is therefore an object of the present invention to provide a spectrophotometric measuring apparatus and method having a high optical density upper limit compared to prior art automated analyzers and which is suitable for testing of successive liquid samples.

Briefly stated in accordance with the present invention, there is provided in a chemical testing apparatus a spectrophotometric measuring apparatus including a cuvette through which liquid sample is pumped having an internal dimension such that a meniscus of a leading edge of a liquid sample is maintained. A radiant energy source and photodetector means are positioned to measure radiant energy transmitted through the liquid across rather than along the path of liquid flow.

BRIEF DESCRIPTION OF THE DRAWINGS

The means by which the foregoing objects and features of invention are achieved are pointed out in the claims forming the concluding portion of the specification. The invention, both as to its organization and manner of operation, may be further understood by reference to the following description taken in connection with the following drawings.

Of the drawings.

DESCRIPTION OF THE PREFERRED EMBODIMENT

Figure 1:
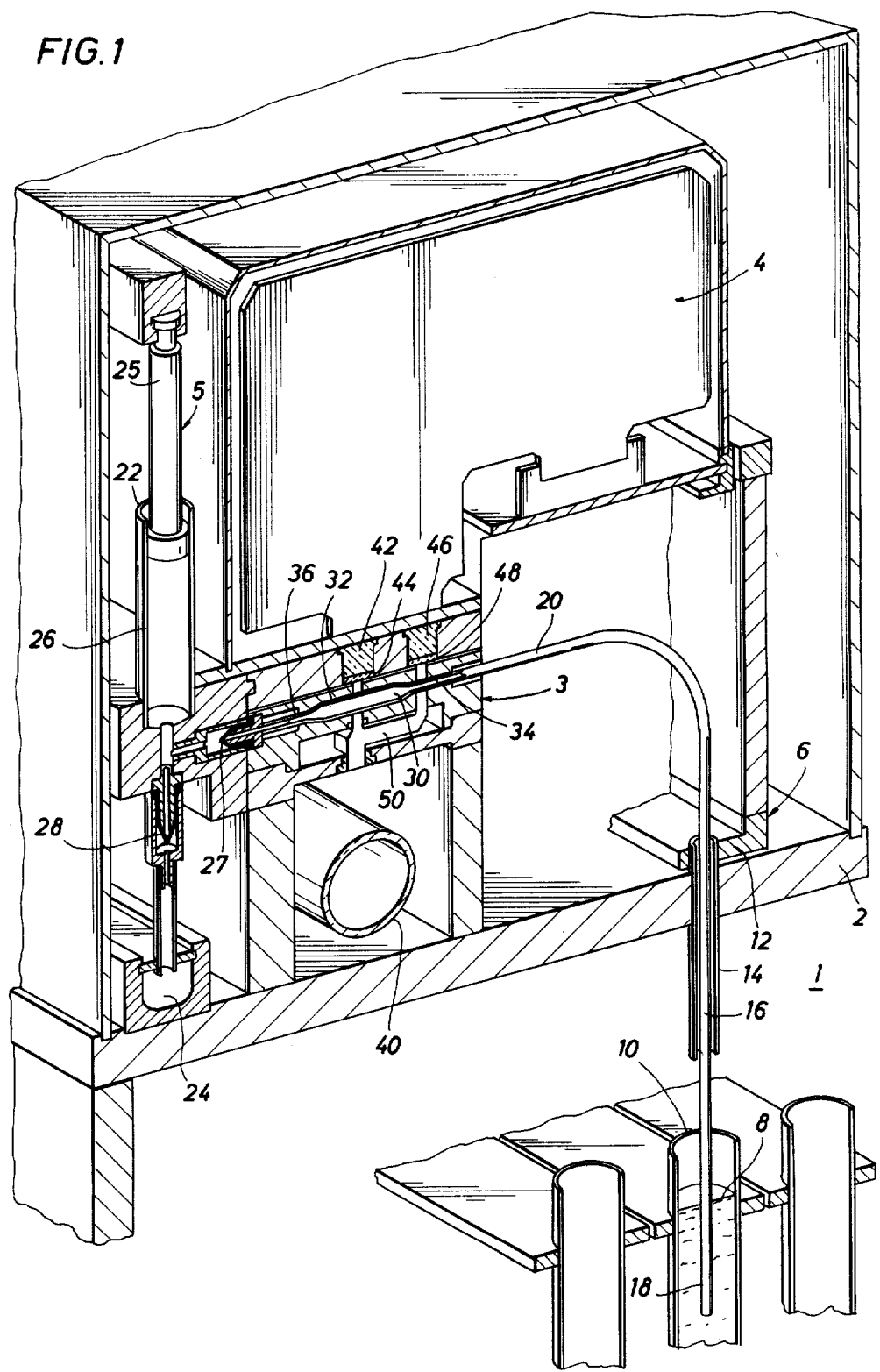
FIG. 1 is a cross-sectional view of a readout station of an automatic chemical testing apparatus incorporating the present invention.

FIG. 1 is a cross-section of an axonometric view of the present invention incorporated in an analysis station 1 of an automatic chemical testing apparatus. The analysis station 1 as illustrated could be incorporated in the automatic chemical testing apparatus according to any of the above-cited patents to Moran. Details of auxiliary functions such as moving liquid sample to the testing apparatus and control of operation of an analysis station are disclosed in thse patents. Alternatively, the apparatus of the present invention may be incorporated in a stand-alone chemical liquid sample analyzer. Inside a housing 2 are mounted spectrophotometric means 3, signal processing circuitry 4, liquid means 5 and liquid sample aspiration means 6. The liquid sample aspiration means 6 aspirates liquid sample 8 from a reaction container 10. The liquid sample 8 comprises reacted contents. The contents may, for example, be an aliquot of biological fluid from a test sample such as blood serum mixed with reagents to test for a particular substance in the serum. The liquid sample 8 generally will have been incubated for a predetermined time so that the reaction therein will have reached an end point. Alternatively, for a kinetic determination in which a number of readings will be made by the spectrophotometric means 3 over a preselected period of time, the reaction may still be ongoing.

The aspiration means 6 includes vertically, reciprocally, moveable bracket 12 having a collar 14 mounted therein which receives a conduit 16 having an inlet and 18 for immersion in sample liquid 8 and an outlet in 20 for connection to the spectrophotometric means 3. The bracket 12 is operable as described in the above-referred to patents to place the inlet 18 of the conduit 16 in a reaction container 10, remove it therefrom at a predetermined later time and move the conduit 16 into a next reaction container 10 for analysis of a next liquid sample 8. The signal processing circuitry for preferably comprises a well-known log ratio detector circuit and signal processing circuitry as in is well-known in the art. Examples of such circuitry are found in U.S. Pat. No. 3,873,273 and 4,061,469, the first aforesaid patent being issued to J. J. Moran, S. Wolff and H. W. Ashley and the latter being issued to C. R. DuBose, both being assigned to the assignee herein and having their disclosures incorporated herein by reference. The liquid transfer means 5 includes a pump 22 operable for periodically drawing liquid into the pump 22 such that liquid already measured is already dropped out of the spectrophotometer apparatus 3 and fresh liquid from a next sample is drawn therein. The pump 22 is operable in the other direction to expel liquid therefrom into a waste conduit 24. The pump 22 may, for example, comprise a piston 25 and cylinder 26 with check valves 27 and 28 connected at its inlet and outlet respectively.

Figure 2:
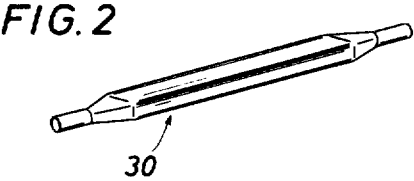
FIG. 2 is an axonometric view of a cuvette which may be used in the embodiment of FIG. 1.

Referring to the spectrophotometric means 3 in greater detail, there is provided a cuvette 30 which is also illustrated in FIG. 2 in axonometric form. The cuvette 22 is made of an optically transmissive substance in the wavelength of the interest. A commonly preferred material is quartz. In the preferred form, the cuvette 30 has a central portion 32 comprising a right square cylinder of a first interior dimension and inlet and outlet portions 34 and 36 of a smaller diameter. "Square" means that the shape is substantially square to the extent permitted by molding techniques for cuvette material. The desired feature is the provision of flat surfaces for the entry and exit of radiant energy. Provision of sharp corners in the interior of the cuvette would be undesirable. Tapered portions connect the center portion 32 to the inlet and outlet portions 34 and 36. Other shapes may be provided. The cuvette 30 is provided with an inner dimension such that a liquid meniscus of a leading edge of sample liquid flowing therethrough is maintained. The maximum size of this dimension is, of course, a function of liquid viscosity. Generally, liquid samples 8 comprising blood serum and other reagents will not have viscosity greatly different from that of water. Therefore a maximum permissible inner dimension of the cuvette 30 depending on the liquid is approximately 0.35 centimeters or, for a more viscous sample, 0.4 centimeters. The inlet and outlet ends 34 and 36 are respectively connected to the conduit 16 and the pump 22 such that a non-turbulent fluid flow therein results. In this manner, the meniscus is maintained.

A radiant energy source 40 is placed on one side of the cuvette 30. The radiant energy source 40 may be any well-known spectrophotometric source. The most commonly used radiant energy sources emit either visible or ultraviolet light. In the preferred embodiment, the radiant energy source 40 is a fluorescent tube emitting a plurality of wavelengths. Consequently, the source 40 may be a source for a plurality of spectrophotometric means 3 all included in one analysis station 1. On an opposite side of the cuvette 30 from the radiant energy source 40 is mounted a first radiant energy detector 42 which provides an output to the signal processing circuitry 4. A wavelength filter 44 is provided between the radiant energy detector 42 and the cuvette 30 to transmit radiation in the wavelength of interest for the particular test being conducted. The radiant energy detector 42 detects radiant energy transmitted through sample liquid in the cuvette 30. Also provided is a second radiant energy detector 46 further comprising a wavelength filter 48 for the same wavelength as that of the wavelength filter 44. The radiant energy detector 46 provides the well-known reference function to measure radiation at the selected wavelength from the source 40. Well-known forms of the radiant energy detectors 42 and 46 comprise P-I-N diodes. The light pipe apparatus 50, comprising, for example, fiber optics transmissive fibers or reflective light guides couples radiation from the source 40 through the cuvette 8 to the filter 44 and detector 42 and from the source 40 to the filter 48 and the detector 46.

Preferably, the radiant energy is directed perpendicular to the transverse axis of the cuvette 32, which is also coincident with the fluid flow path. As opposed to the most common forms of prior art, spectrophotometer apparatus in which sample liquid flows through a cell, in accordance with the present invention, radiant energy is directed across the fluid flow path and not therealong. Thus fluid flow is along a longitudinal axis of the elongated cuvette 30, and radiant energy is directed along a transverse dimension.

Figure 3:
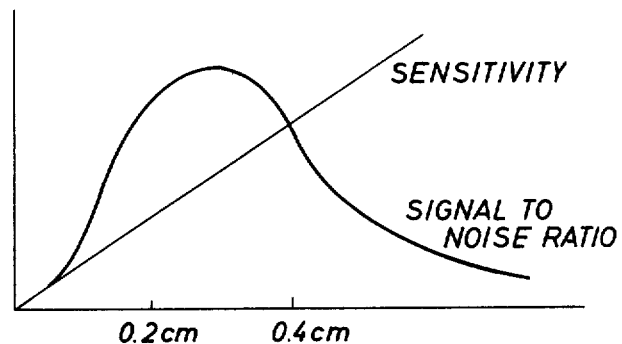
FIG. 3 is a chart of both sensitivity and signal to noise ratio versus optical pathlength, useful in understanding the operation of the present invention.

A significant effect of this measurement is increased signal to noise ratio. This is explained with respect to FIG. 3 which is a plot of both sensitivity and signal to noise ratio, both in arbitrary units, versus optical pathlength. Sensitivity here is defined as change in voltage output for nominal signal processing circuitry 4 for a change in optical density value of a preselected level. The longer the pathlength, the greater the voltage change. However, a change of unity of optical density of a liquid sample 8 in a cuvette 30 provides attenuation by a factor of 10. Therefore very low energy levels will be provided to the detector 42. By use of a shorter energy path in accordance with the present invention, a radiant energy much less attenuated is provided to the detector 42. Signal to noise ratio is thus improved. Therefore, high levels of amplification may be provided in the signal processing circuitry 4 to restore sensitivity. An increased range of optical density measurement capability is provided. An upper limit of approximately 5 O.D. is provided, while the traditional one centimeter path provides for an upper capability of about 2 O.D. A thousandfold increase in optical absorbence measurement range is provided. However, it has been found that an optical pathlength through the cuvette 30 of less than 0.2 cm may decrease sensitivity too far so as to again decrease signal to noise ratio.

The present construction provides for improved utilization of chemistries in an automatic chemical testing apparatus. An example is a blood urea nitrogen bichromatic ultraviolet chemistry. This chemistry initially has a high optical density value of the liquid sample 8. In prior art apparatus, an extra dilution step of the liquid sample 8 would be required to reduce optical density to a measurable value. In the present apparatus, automatic measurement may be performed directly.

Figure 4:
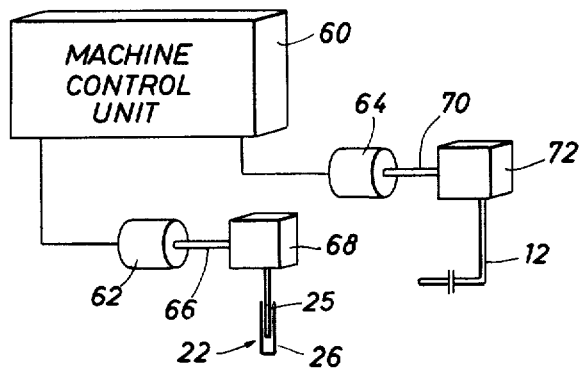
FIG. 4 is a schematic diagram of liquid transfer operating means.

In order to reduce intersample carryover, the apparatus of FIG. 4 is utilized to provide rinsing of the cuvette 30 by initial portions of a next liquid sample 8 to remove remaining traces of a previous liquid sample 8. FIG. 4 is a schematic diagram of fluid transfer operating means. The same reference numerals are used to denote elements corresponding to those in FIG. 1. In FIG. 4, a machine control unit 60, such as that in the above-cited patents to Moran is provided which has outputs connected to first and second reversible motors 62 and 64. The motor 62 has a driveshaft 66 connected to a linkage unit 68 for raising and lowering the piston 25 of the pump 22. The motor 64 has a driveshaft 70 connected to a linkage unit 72 for lowering and raising the bracket 12, whereby the inlet 18 of the conduit 16 is moved into and out of sample liquid 8 in a reaction container 10.

Figure 5:
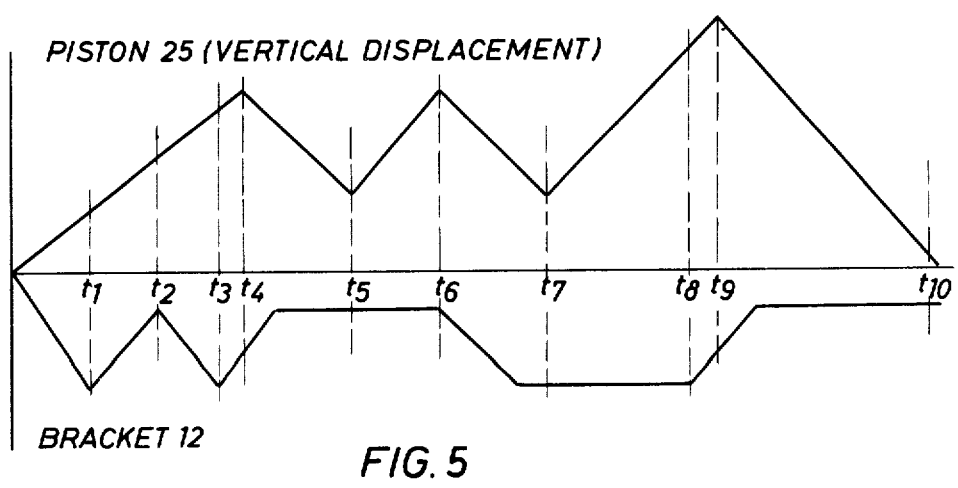
FIG. 5 is a timing chart illustrating one form of operation of the circuit of FIG. 4.

Operation is explained with respect to FIG. 5, which is a timing chart. The ordinate is vertical displacements of the piston 25 and bracket 12, and the abscissa is time. At time $t_0$, the control unit 60 provides a signal to the motor 64 to lower the bracket 12. At time $t_1$, the motor 64 is reversed to raise the conduit 16 to its "home position" above the sample level in the reaction container 10. At time $t_3$, the motor 64 is reversed again. Simultaneously, from time $t_0$ to $t_4$, the machine control unit 60 provides a signal to the motor 62 to raise the piston 25. In the preferred embodiment, the components are proportioned such that about 0.2 ml. of sample liquid 8 enters the conduit 16 preceded by a small amount of air and followed at time $t_2$ by about 0.2 ml. of air. At time $t_3$, another 0.2 ml. of sample liquid 8 enters the conduit 16 followed by air. At time $t_4$, the first 0.2 ml. of sample liquid 8 fills the cuvette 30. At time $t_4$, the machine control unit 60 reverses the motor 62 to lower the piston 25. Liquid in the piston 26 exists to the drain 24 through the check valve 28. At time $t_5$, the motor 62 is reversed, and the piston 25 is again raised. From times $t_4$ to $t_5$, which may be one second, the first 0.2 ml liquid portion is mixed with liquid if any previously in the cuvette 30. From times $t_5$ to $t_6$, the first 0.2 ml. portion is drawn into the pump 22, and the 0.2 ml. air interface passes therethrough, and the second 0.2 ml. liquid portion fills the cuvette 30 for a second rinsing action. At time $t_6$, the motor 62 is reversed, and liquid is expelled from the pump 22 out the check valve 28. A time $t_6$, the control unit 60 operates the motor 64 to lower the bracket 12 so the inlet 18 of the conduit 16 is again in the sample liquid 8 in the reaction container 10. At time $t_7$, the motor 62 is operated to raise the piston 25 approximately twice the distance as in the previous operation raising the piston 25. Approximately 0.4 ml. of liquid is moved into the conduit 16 and cuvette 30 to assure a completely filled lightpath. At time $t_8$, the motor 64 is operated to raise the bracket 12 to its home position again and provides an air interface in the conduit 16. At time $t_9$, the motor 62 is operated to lower the piston 25 again. Since in a nominal sample there may be three percent carryover from one filling of the cuvette 30 to the next, performing the above-described measurement on a third liquid portion of a liquid sample 8 as described above effectively eliminates carryover. Carryover is on the order of a quarter of one percent, which should not be a significant amount in the context of clinical chemistry measurements. Other timing cycles to provide for successive rinses of the cuvette 30 and air interfaces therebetween may be provided.

The foregoing teachings should enable those skilled in the art to provide many forms of spectrophotometric measuring apparatus constructed in accordance with the present invention.

What is claimed as new and desired to be secured by Letters Patent of the United States is:

1. In an analysis station in a chemical testing apparatus, spectrophotometric measuring apparatus comprising a substantially horizontal elongated optically transmissive cuvette defining a liquid sample flow path along a longitudinal axis, conduit means connected for supplying liquid sample from a reaction container to said cuvette, said conduit means being coupled in a taper to said cuvette to provide a non-turbulent fluid path transition, said cuvette having a pair of parallel opposed flat surfaces along said longitudinal axis separated by an internal dimension no greater than that which will maintain a meniscus at a leading edge of liquid sample when said liquid sample statically occupies said cuvette, a radiant energy source positioned for directing energy through said cuvette along a path substantially perpendicular to said flat surfaces, and first radiant energy detection means positioned for receiving energy directed through said cuvette.

2. Apparatus according to claim 1 further comprising a second radiant energy detector means and means directing radiant energy directly from said source to said second radiant energy detector means.

3. Apparatus according to claim 2 wherein each of said radiant energy detector means comprises a wavelength filter for a particular wavelength and wherein said radiant energy sources comprises a fluorescent lamp emitting radiant energy at a plurality of wavelengths including the particular wavelength.

4. Apparatus according to claim 3 wherein said cuvette comprises a right square cylinder and wherein said liquid sample flow path is along a longitudinal axis of said cylinder.

5. Apparatus according to claim 4 wherein said cuvette comprises an inlet end, an outlet end and a central portion and wherein said cuvette tapers from a first inner transverse dimension to a smaller inner transverse dimension from said central portion to said inlet and said outlet ends.

6. Apparatus according to claim 5 comprising pumping means coupled to the outlet end of said cuvette.

7. Apparatus according to claim 6 wherein the optical path length of radiant energy through said cuvette is between 0.2 and 0.35 cm.

8. Apparatus according to claim 1 wherein the internal dimension of said cuvette is between 0.2 and 0.35 cm.

9. Apparatus according to claim 6 or claim 7 wherein said pumping means comprises means for moving at least one liquid portion into and out of said cuvette and moving liquid sample into said cuvette for measurement.

10. A method of analyzing a sample liquid in a chemical testing apparatus comprising the steps of providing a substantially horizontal elongated optically transmissive cuvette defining a liquid flowpath along a longitudinal axis and having a pair of parallel opposed flat surfaces along said longitudinal axis separated by an internal dimension no greater than that which will maintain a meniscus of a leading edge of liquid sample statically occupying said cuvette, moving a liquid having a leading edge defining a meniscus into said cuvette, maintaining said liquid in said cuvette for a predetermined period of time, moving said liquid from said cuvette and moving a sample liquid having a leading edge defining a meniscus into said cuvette, maintaining said sample liquid in said cuvette for a predetermined period of time, directing radiant energy through said sample liquid along a path substantially perpendicular to said flat surfaces of said cuvette while said sample liquid statically occupies said cuvette, and measuring the radiant energy transmitted from said cuvette.

11. The method of claim 10 wherein the step of directing radiant energy comprises providing a radiant energy source and a radiant energy detector on opposite transverse sides of said cuvette and directing radiant energy substantially perpendicularly to said longitudinal axis.

12. The method of claim 10 or claim 11 further comprising the step of creating an air interface between said first portion of said sample liquid and said second portion of said sample liquid.

13. Apparatus according to claim 1 wherein said cuvette comprises an inlet end, an outlet end and a central portion and wherein said cuvette tapers from a first inner transverse dimension to a smaller inner transverse dimension from said central portion to said inlet and said outlet ends.

14. Apparatus according to claim 13 wherein said first inner dimension is between 0.2 and 0.35 cm.

15. A method of analyzing a sample liquid in a chemical testing apparatus comprising the steps of providing a substantially horizontal elongated optically transmissive cuvette defining a flow path along a longitudinal axis and having a pair of parallel opposed flat surfaces along said longitudinal axis separated by an internal dimension no greater than that which will maintain a meniscus of a leading edge of liquid statically occupying said cuvette, pumping a first portion of liquid into said cuvette, maintaining said liquid in said cuvette for a predetermined period of time, creating an air interface between said first portion of liquid and a second portion of liquid whereby a meniscus is defined at a leading edge of said second liquid portion, pumping said second portion of liquid into said cuvette, maintaining said second portion of liquid in said cuvette for a predetermined period of time, creating an air interface between said second portion of the liquid and a liquid sample whereby a meniscus is defined at a leading edge of the liquid sample, pumping said second portion of liquid out of said cuvette and said liquid sample into said cuvette, maintaining said liquid sample in said cuvette for a predetermined period of time, directing radiant energy through said sample liquid along a path substantially perpendicular to said flat surfaces while said liquid sample statically occupies and cuvette, and measuring the radiant energy transmitted from said cuvette.

16. The method of claim 15 further comprising the step of providing a cuvette having an inlet end, and outlet end and a central portion wherein said cuvette tapers from a first inner transverse dimension to a smaller inner transverse dimension from said central portion of said inlet and said outlet ends.

* * * * *